US011925382B2

(12) United States Patent
Mascarell et al.

(10) Patent No.: US 11,925,382 B2
(45) Date of Patent: Mar. 12, 2024

(54) CORING DEVICE AND CORING AND INSERTION ASSEMBLY COMPRISING SUCH A DEVICE

(71) Applicant: FINEHEART, Pessac (FR)

(72) Inventors: Arnaud Mascarell, Montbazon (FR); Stéphane Garrigue, Begles (FR)

(73) Assignee: FINEHART, Pessac (FR)

( * ) Notice: Subject to any disclaimer, the term of this patent is extended or adjusted under 35 U.S.C. 154(b) by 475 days.

(21) Appl. No.: 17/057,211

(22) PCT Filed: May 22, 2019

(86) PCT No.: PCT/FR2019/051161
§ 371 (c)(1),
(2) Date: Nov. 20, 2020

(87) PCT Pub. No.: WO2019/224477
PCT Pub. Date: Nov. 28, 2019

(65) Prior Publication Data
US 2021/0212718 A1    Jul. 15, 2021

(30) Foreign Application Priority Data

May 22, 2018    (FR) ...................................... 1854238

(51) Int. Cl.
*A61B 17/3205*    (2006.01)
*A61B 17/00*    (2006.01)
*A61B 17/34*    (2006.01)

(52) U.S. Cl.
CPC .. *A61B 17/32053* (2013.01); *A61B 17/00234* (2013.01); *A61B 17/3423* (2013.01);
(Continued)

(58) Field of Classification Search
CPC ........ A61B 17/32053; A61B 17/00234; A61B 17/3423; A61B 17/320016;
(Continued)

(56) References Cited

U.S. PATENT DOCUMENTS 11,259,827 B2 *    3/2022    Trueba ............. A61B 17/32053
2007/0167968 A1    7/2007    Pandey
(Continued)

FOREIGN PATENT DOCUMENTS

WO    2014117087    7/2014

OTHER PUBLICATIONS

International Search Report issued on International Patent Application No. PCT/FR2019/051161 dated Aug. 30, 2019.

*Primary Examiner* — Julian W Woo
(74) *Attorney, Agent, or Firm* — Perman & Green, LLP (57) ABSTRACT

A coring device, for forming an opening in a tissue wall, includes a body having a proximal end, a distal end and an internal housing, a coring head having a transection blade and being movable between a rest position and an actuated position, an actuation mechanism for moving the head between the positions and having an actuation rod, at one end of which the head is placed, a lumen extending through at least the proximal end of the body, actuation rod and coring head in order to allow passage of a flexible guide element, and the distal end of the body forms a support for a surgical tool configured to receive a hollow surgical tool with a positive fit and to support this tool to permit linear guiding of the surgical tool during the movement of the latter toward the outside of the coring device.

13 Claims, 7 Drawing Sheets

(52) U.S. Cl.
CPC ............... *A61B 2017/00252* (2013.01); *A61B 2017/3419* (2013.01); *A61B 2017/3425* (2013.01); *A61B 2017/3484* (2013.01); *A61B 2017/3492* (2013.01)

(58) Field of Classification Search
CPC .. A61B 2017/00252; A61B 2017/3419; A61B 2017/3425; A61B 2017/3484; A61B 2017/3492; A61B 2017/00247; A61M 60/178; A61M 60/216; A61M 60/863
USPC .................................................. 606/185, 184
See application file for complete search history.

(56) References Cited

U.S. PATENT DOCUMENTS

| | | |
|---|---|---|
| 2009/0082778 A1 | 3/2009 | Beane et al. |
| 2012/0296358 A1* | 11/2012 | Nguyen .............. A61M 60/232 606/170 |
| 2016/0121033 A1 | 5/2016 | Cotter et al. |
| 2017/0202575 A1* | 7/2017 | Stanfield ............... A61M 29/00 |
| 2018/0296212 A1 | 10/2018 | Jimenez et al. |

* cited by examiner

CORING DEVICE AND CORING AND INSERTION ASSEMBLY COMPRISING SUCH A DEVICE

CROSS REFERENCE TO RELATED APPLICATIONS

This application is a National Stage of International Application No. PCT/FR2019/051161, having an International Filing Date of 22 May 2019, which designated the United States of America, and which International Application was published under PCT Article 21(2) as WO Publication No. 2019/224477 A1, which claims priority from and the benefit of French Patent Application No. 1854238, filed on 22 May 2018, the disclosures of which are incorporated herein by reference in their entireties.

BACKGROUND

1. Field

The present disclosure relates to a coring device for forming an opening in a tissue wall, in particular with a view to placing a cardiac pump on a beating heart.

It also relates to an assembly for coring a wall of a beating heart and for inserting a portion of a device for anchoring a cardiac pump through the opening formed by coring.

2. Brief Description of Related Developments

Heart failure (HF) is a pathological state in which the heart of a patient is unable to provide a rate of blood flow necessary for the metabolic needs of the body.

It is known to treat heart failure by implanting a ventricular assist device (VAD), which is an artificial cardiac pump.

This mechanical pump does not replace the heart, which continues to function, but helps the weakened ventricle to increase the rate of blood flow in order to meet the needs of the individual.

This assistance may be temporary while waiting for a graft to become available for a heart transplant.

However, a significant proportion of patients will not receive such a transplant, either because they may not be candidates for such a transplant, for example because of severe heart failure, or because no suitable graft is available for these patients.

In that case, ventricular assistance is used as the intended solution, which is to say that the artificial cardiac pump is implanted for the long term.

These cardiac pumps are therefore the subject of intensive research aimed at improving the survival and the quality of life of patients presenting with heart failure.

Many advances have been made in recent years, and today we have ventricular assist devices which are more compact and quieter and which provide an increased service life.

The implantable cardiac pumps of the prior art are thus typically equipped with an integrated electric motor to ensure their operation, the speed of rotation of the pump providing the force necessary for circulating the blood from the weakened ventricle to the circulatory system.

Systems for implanting such pumps in an opening of a ventricular wall are known.

These implantation systems generally comprise a tubular portion, at the ends of which are placed, or formed, collars which are intended to be each pressed against an opposite face of the ventricular wall after insertion of the tubular portion into an opening made in this ventricular wall with a coring device.

These collars thus make it possible to maintain this hollow tubular portion in position, which then defines an open conduit passing through the ventricular wall.

At the end, placed outside the heart, of this tubular portion, a suction pump is inserted which, once fitted, ensures that the blood present in the ventricle returns to the circulatory system.

Although representing some progress in terms of the quality of life of a patient suffering from heart failure, there are still many disadvantages.

In particular, forming this opening on a beating heart in order to minimize the side effects of the intervention on the patient can lead to significant blood loss during the implantation of the cardiac pump.

Important factors for achieving a successful outcome therefore include great dexterity and speed of action on the part of the practitioners, all of which places a strain on the team performing the intervention.

In addition, with the dimensions of the collars being reduced in order to facilitate their passage through the opening made in the ventricular wall, the mechanical strength of the implantation system is limited. For example, it does not allow significant forces to be applied to it once it is in place on the ventricular wall.

In addition, it is desirable that the blood ejection end of the pump is centered on the cardiac valve in order to ensure an optimal flow of ejected blood.

The positioning of the opening in the ventricular wall thus influences the actual performance of the cardiac pump in ejecting blood into the aorta.

However, in the absence of markers, it has been found that this opening is not always well positioned with respect to the cardiac valve. The flow of ejected blood is therefore not optimal.

There is therefore an urgent need for a coring device whose novel design overcomes the disadvantages described above.

SUMMARY

The present disclosure aims to overcome the disadvantages of the prior art and to meet the above demands by making available a coring device for coring a tissue wall, which device is simple in terms of its design and operating mode and is reliable and particularly easy for a practitioner to handle.

Another object of the present disclosure is to make available such a coring device which offers several functions and which in particular is configured to receive, support and center an assistance tool for placement of an anchoring device part with respect to the opening that has been formed by coring.

Yet another object of the present disclosure is to make available such a coring device with which it is possible to align the coring head during the formation of the opening in the tissue wall, in order to ensure optimal positioning of the opening formed in the tissue wall with respect to the heart valve.

The present disclosure also aims to provide an assembly for coring a wall of a beating heart and for inserting a portion of a device for anchoring a cardiac pump through the opening made by coring, thus ensuring easier placement of this portion of the anchoring device and thereby permitting maximization of its dimensions.

Another object of the present disclosure is to make available such an assembly that limits the risk of blood loss for the patient.

To this end, the disclosure relates to a coring device for forming an opening in a tissue wall, this device comprising:
- a body having a longitudinal axis, said body having a proximal end and a distal end, said body having an internal recess,
- a coring head having a transection blade, this head being movable between a rest position and an actuated position, said coring head having a coring axis,
- an actuation mechanism for moving said head between said positions, said mechanism having an actuation rod, at one end of which said movable head is placed, and
- the distal end of said body forms a support for a surgical tool, or surgical accessory, this tool support being configured,
- on the one hand, to receive a hollow surgical tool by positive engagement and to support this tool, this surgical tool then surrounding the distal end of said body when it is placed on said tool support, by being coaxial with said coring axis, and,
- on the other hand, to permit linear or substantially linear guiding of said surgical tool during the movement of the latter toward the outside of the coring device.

Advantageously, such a coring device not only makes it possible to form an opening in a tissue wall but also to insert, into the opening made, the distal end of a surgical tool, for example a tool for assisting in the placement of an anchoring device part, which saves time, enhances comfort for the surgical team and increases patient safety.

It is in fact not necessary for a practitioner, other than the one having formed the opening, to intervene quickly after formation thereof in order to insert the surgical tool or accessory, and there is no change of surgical equipment.

Such a device also makes it possible to insert this surgical tool into the opening made, since the configuration of this tool support ensures an alignment, or coincidence, of this opening and of the distal end of the surgical tool, which is configured to pass through this opening.

Such a coring device is particularly useful for forming an opening in a ventricular wall of a beating heart for the placement and connection of an anchoring ring, also known as an anchoring device or fixation device, of a cardiac pump in this opening.

Such an anchoring ring typically comprises a ring part comprising a hollow body, at the end of which is placed a membrane that is self-expanding between a first configuration, called a deformed configuration, in which it has a tubular or substantially tubular shape, and a second configuration, called the initial configuration, in which it defines a flange, or collar, extending radially, or substantially radially, from said hollow body, said flange being intended to abut against an inner face of said ventricular wall of the beating heart.

The surgical tool is then advantageously a hollow body of generally cylindrical shape configured to be received in the opening made in the ventricular wall and to keep this opening open to its maximum dimensions in order to facilitate the insertion of at least the self-expanding membrane into the ventricular chamber.

In various particular embodiments of this device, each having its particular advantages and susceptible of many possible technical combinations:

this coring device has a lumen extending through at least the proximal end of said body, said actuation rod and said coring head in order to allow the passage of a flexible guide element.

The use of a flexible guide element, such as a guidewire, passing through the ventricular wall and the corresponding cardiac valve, for example the aortic valve, allows the opening made in the ventricular wall to be aligned with this cardiac valve.

Advantageously, such an alignment ensures, from the outset, an optimal centering of the pump body on this cardiac valve, and therefore good performance in terms of ejection of blood through the cardiac valve.

Preferably, this lumen supports such a flexible guide element said tool support has an outer peripheral wall which is tubular and of a diameter equal to or substantially equal to the diameter of said transection blade.

Here, the term "substantially equal" means that this diameter may vary by a few percent in relation to the diameter of the opening made in the ventricular wall.

The hollow surgical tool is then at least partly of tubular or substantially tubular shape, having an internal diameter equal to or substantially equal to the diameter of said transection blade, so that this surgical tool can slide along said movable head when it is introduced onto or removed from the tool support.

said tissue wall being a wall of a beating heart for receiving a device for anchoring a cardiac pump comprising a flange, or collar, to be pressed against the outer surface of said beating heart wall, the length of said tool support is at least equal to the sum of the thickness of said tissue wall and the thickness, or longitudinal dimension, of said flange, or collar, intended to be placed against the outer surface of the wall of said heart.

the device has one part of an indexing means, said surgical tool being intended to carry the complementary part of this indexing means, in order to align said surgical tool on said tool support.

Purely by way of illustration, the device can comprise a lug intended to be received in a corresponding housing placed on the edge of the proximal end of the surgical tool.

the device has a stop for stopping the movement of said surgical tool along said longitudinal axis and in the direction of said proximal end, such that the surgical tool remains positioned on said tool support.

said body has two body parts engaged one inside the other, a first body part being movable in translation relative to the other body part, such that its movement in and out of the other body part causes the translation movement of said coring head.

Preferably, each body part has a gripping handle. Advantageously, said actuation mechanism comprises a guide carriage supporting said actuation rod and received in said internal housing, this housing being configured to form a guide rail for translation of said guide carriage, said guide carriage being rigidly connected to said first body part movable in translation.

The present disclosure also relates to an assembly for placement of a tool or of a surgical accessory in a tissue wall. According to the disclosure, this assembly comprises:
- a coring device as described above, and
- a hollow surgical tool or accessory configured to be engaged on the distal end of said coring device while leaving said coring head free.

According to one embodiment of the assembly of the disclosure, said surgical tool or accessory has, at its distal end, a tubular or substantially tubular portion configured to maintain the shape and diameter of the opening formed by coring in the tissue wall.

Preferably, this tubular or substantially tubular portion has a length at least equal to the thickness of the tissue wall.

According to another embodiment of the assembly of the disclosure, with the body of the coring device having one part of an indexing means, this surgical tool or accessory has a complementary part of this indexing means, in order to align said surgical tool or accessory on said tool support.

According to yet another embodiment, with said surgical tool or accessory being a tool assisting the placement of a device for anchoring a cardiac pump through an opening made by coring in the wall of a heart, said hollow assistance tool delimits an internal channel for the passage of said anchoring device, the diameter of which is substantially equal to the diameter of this opening.

Advantageously, said tubular or substantially tubular portion of this assistance tool has a length at least equal to the sum of the thickness of the wall of said heart and the thickness, or longitudinal dimension, of a flange, or collar, intended to be connected to the outer surface of the wall of said heart.

Preferably, with the body of the coring device having one part of an indexing means, this assistance device has a complementary part of this indexing means, in order to align said surgical tool on said tool support in a predefined configuration. For example, this predefined arrangement of the surgical tool ensures its alignment with respect to a flange, or collar, assembled against the outer surface of the wall of said heart.

Preferably, with this flange, or collar, being intended to be placed against the outer surface of the wall of said heart and comprising at least one protrusion, or stub, placed on its lateral face, said surgical tool has, for each protrusion, an open groove intended to receive said corresponding protrusion, or stub, said groove being configured to ensure, by rotation of said surgical tool about the coring axis, a locking of said surgical tool on said flange or collar.

According to yet another embodiment of the assembly of the disclosure, this assembly has an elongate pusher device having, at its distal end, a support head for supporting an anchoring device part comprising said flange, or collar, in its deformed configuration, said head having a means of connection, such as a thread, to said anchoring device part and the latter comprising a complementary connection means in order to ensure the connection of these elements, said elongate pusher device being configured to traverse said surgical tool so that said flange, or collar, of the anchoring ring can pass through the opening made in the wall of said heart.

Preferably, this pusher device has the form of a tube or a rod having a lumen for receiving the flexible guide element.

BRIEF DESCRIPTION OF THE DRAWINGS

Other advantages, aims and particular features of the present disclosure will become clear from the following description, which is provided for explanatory purposes and is non-limiting and in which reference is made to the accompanying drawings, in which.

DETAILED DESCRIPTION

Firstly, it will be noted that the figures are not to scale.

FIGS. 1 to 7 show schematically a coring device 10 for making an opening in the ventricular wall of a beating heart, according to a particular embodiment of the present.

This coring device 10 has two body parts 11, 12 which are engaged one inside the other in such a way that one of these parts is mounted slidably in the other body part. This device has a proximal end and a distal end.

In the context of the present, the term "proximal" means the position closest to the healthcare professional or practitioner, while the term "distal" must be understood here as meaning farthest away from this professional. In other words, the distal end of a component is the end that would be engaged first in the beating heart, while the proximal end of said component would be the last end to be engaged therein.

This coring device 10 comprises a coring head 13 having a tip with a frustoconical shape, at its distal end, in order to facilitate its insertion through an incision, made with a cutting tool such as a scalpel, in the ventricular wall of this beating heart. This head 13 also has a transection blade 14 placed at its proximal end. This transection blade 14 has a straight cross section of circular shape, although it could have other appropriate shapes, for example oval.

This coring head 13 is movable between a rest position, in which the transection blade 14 is pressed against, or is placed near, the distal end of the main body of the coring device 10, and an actuated position, in which the transection blade 14 is placed at a distance from the distal end of the main body of the coring device 10.

More precisely, this coring head 13 is actuated by an actuation mechanism comprising an actuation rod 15, at the end of which this head 13 is mounted, this rod 15 being coupled to an internal housing of the main body of the coring device 10.

This main body here has two body parts 11, 12 engaged one inside the other, a first body part being movable in translation relative to the other body part, such that its movement in and out of the other body part causes the translation movement of said coring head 13.

Each body part has a gripping handle 16, 17 having a longitudinal axis Z. These handles 16, 17 are here arranged in such a way that their longitudinal axis is perpendicular to the longitudinal axis defined by the body of the coring device 10.

Thus, the practitioner can hold with one hand a handle 16 of a first body part 11, while his other hand holds the handle 17 of the other body part 12, in order to easily move these two body parts relative to each other and thus cause the movement of the coring head 13.

Advantageously, the geometric axis or coring axis of the coring device 10 is that of the actuation rod 15 on which the coring head 13 is centered.

The actuation mechanism also comprises a guide carriage 18 supporting the actuation rod 15 and received in the internal housing 19 of the main body. The actuation rod 15 is advantageously centered.

With the guide carriage 18 being rigidly connected to the first body part movable in translation, this internal housing 19 defines a guide rail for translation of this guide carriage.

A lumen 20 extends through the proximal end of the main body of the coring device 10, the actuation rod 15 and the coring head 13 in order to allow the passage of a guide 37. This guide 37 is intended for guiding, in particular aligning, the coring head 13 as the latter approaches the ventricular wall in order to form an opening by coring.

More precisely, this guide 37 is intended to pass through the aortic valve in order to guide the coring device 13 and thus fix the orientation of the opening, to be made by coring, relative to the anatomical location of the aortic valve (or the pulmonary valve if this coring device 13 is used for the right ventricle).

Advantageously, the distal end of the main body of the coring device 10 also forms an accessory support 21.

This accessory support 21 has a tubular outer peripheral wall whose outer diameter is equal to the diameter of the transection blade 14.

Figure 1:
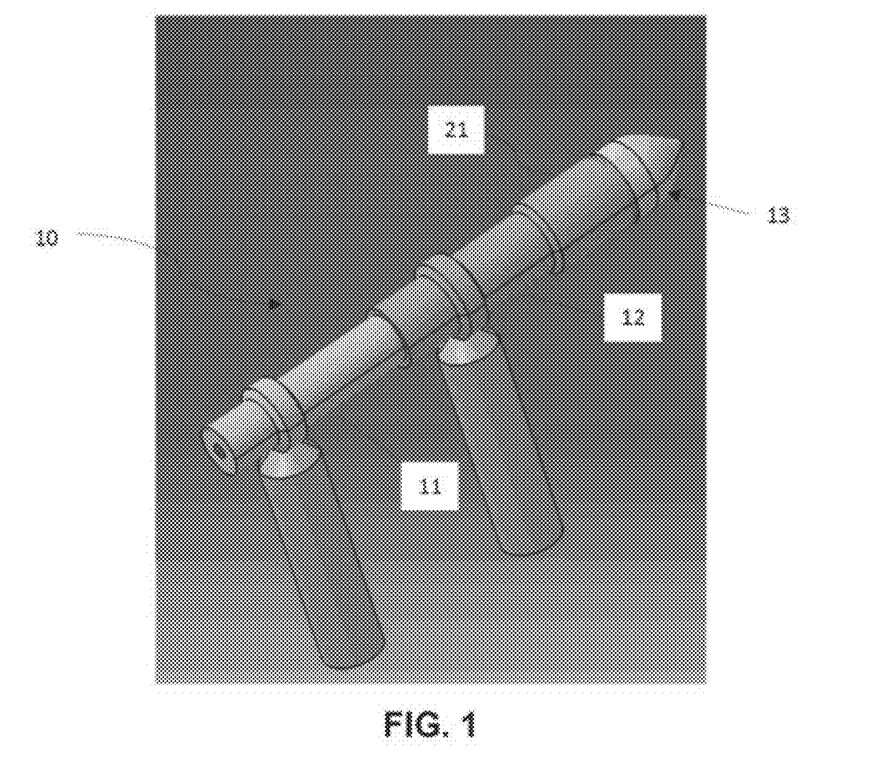
FIG. 1 shows schematically a coring device for making an opening in a ventricular wall of a beating heart, according to a particular embodiment of the present disclosure.
Figure 2:
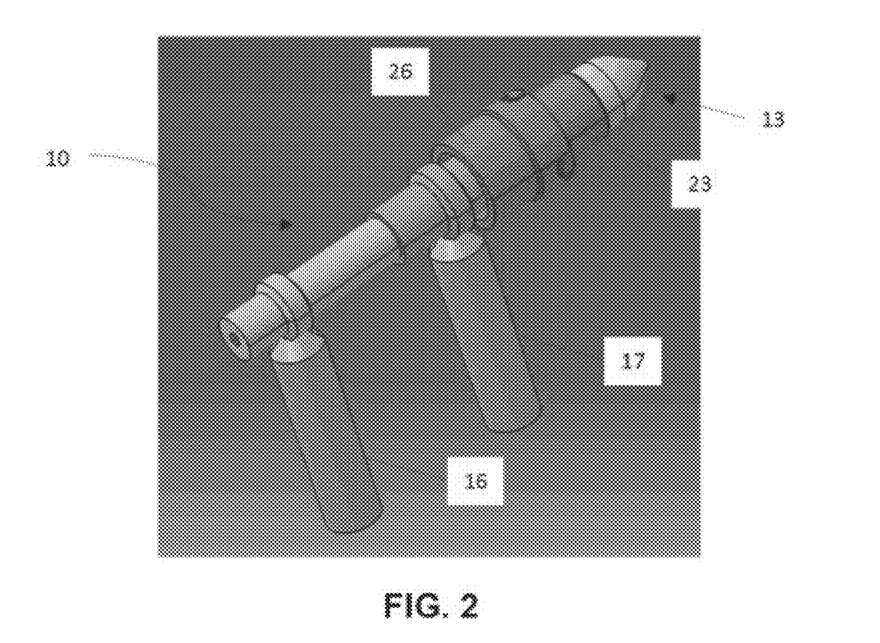
FIG. 2 shows the coring device from FIG. 1, an accessory for assistance in the placement of an anchoring ring being received at the distal end thereof in order to define an assembly for coring and for inserting a part of an anchoring ring of a ventricular assist device.
Figure 3:
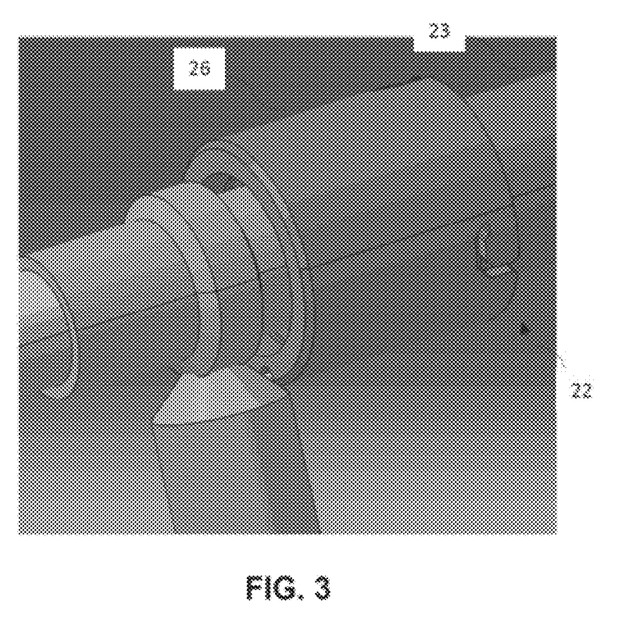
FIG. 3 is a partial and enlarged view of the assembly illustrated in FIG. 2, showing an indexing means for aligning the accessory for placement assistance.
Figure 4:
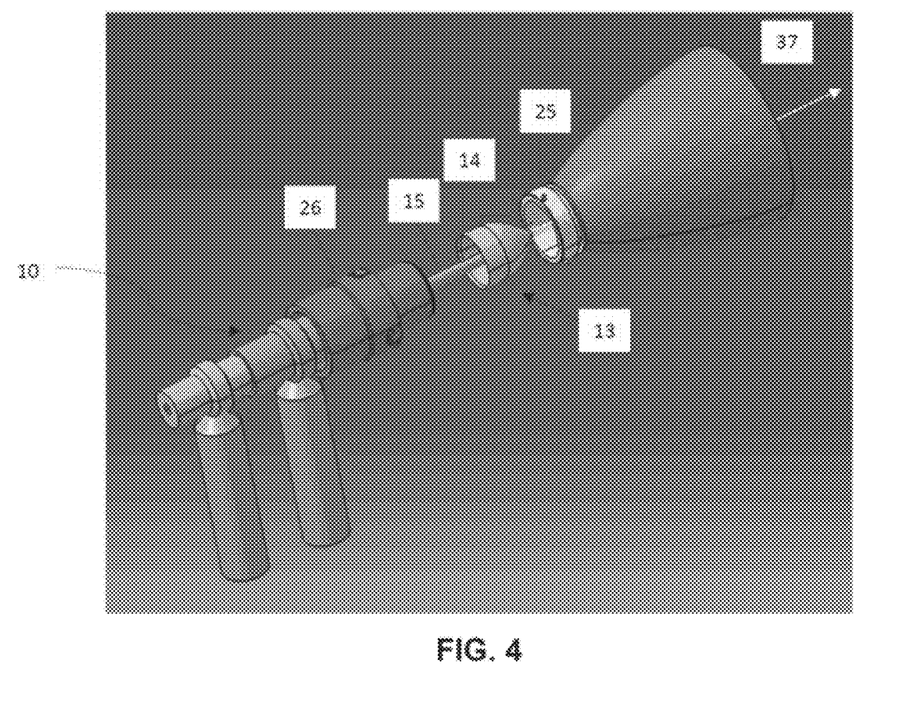
FIG. 4 is a schematic representation of the assembly from FIG. 2, the coring head being in its actuated position for its insertion into a small orifice, previously made with a cutting tool, in the ventricular wall of the heart.

An assistance accessory 22, for assisting in the placement of a part of an anchoring ring of a cardiac pump, is received by positive engagement on this accessory support 21. This assistance accessory 22 is hollow and has a sheath 23 extending from an intermediate portion thereof toward its distal end.

Figure 5:
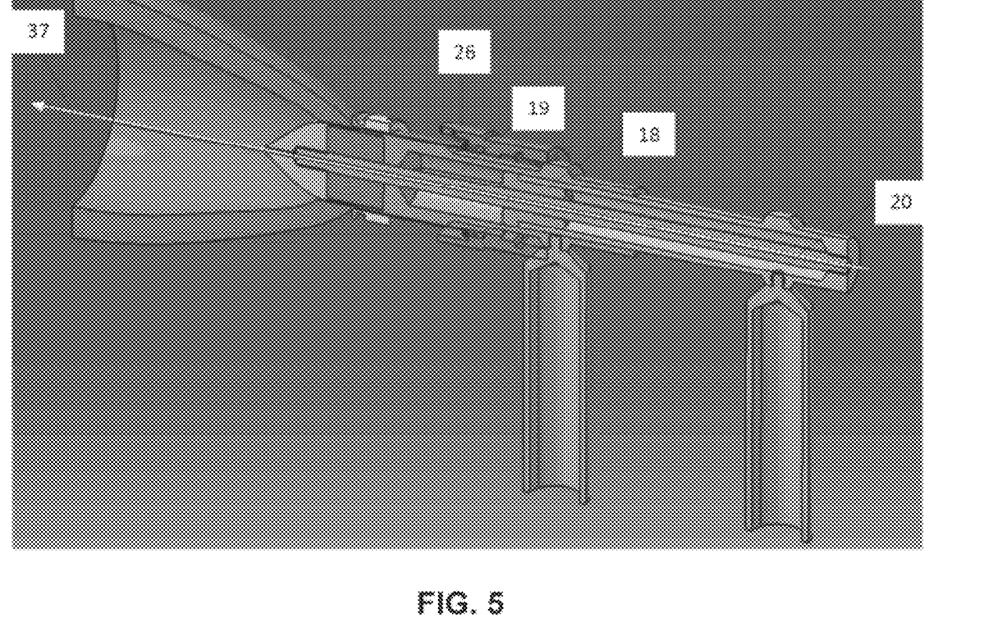
FIG. 5 is a perspective and sectional view of the assembly from FIG. 2, just after the cut has been made in the ventricular wall.

As is shown in FIG. 5, while the coring head 13 is still partially placed in the ventricular chamber, the practitioner can insert, into the opening made in the ventricular wall, a part of the assistance accessory 22, in particular its sheath 23, by moving it in translation on the accessory support 21, which ensures linear guiding.

With this assistance tool being made of a rigid material such as titanium, its sheath 23 maintains the opening at its maximum extension and, with its internal channel, delimits a path for the free passage of an anchoring ring part comprising a tubular portion and, at the distal end of the latter, a self-expanding membrane 24 in its first configuration, i.e. a deformed configuration, in which it has a tubular or substantially tubular shape. This self-expanding membrane 24 is made of Nitinol, for example.

Another flange, or second flange 25, of the anchoring ring having been previously connected, for example by suturing, to the outer surface of the ventricular wall, the assistance accessory 22 has, at its proximal end, a hollow cylindrical connection head 26 forming a protrusion of the sheath 23, partially surrounding the latter. This connection head 26 is intended to be connected to this second flange 25 in order to achieve a removable coupling of the accessory to the assembly composed of the second flange and the apex of the heart. This second flange 25 is made of Dacron, for example.

Figure 6:
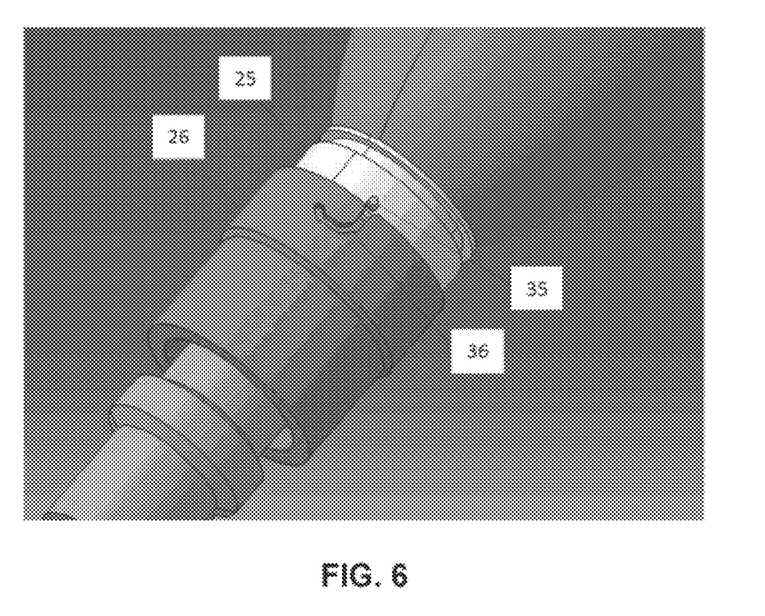
FIG. 6 is a partial top view of the assembly from FIG. 2, during the connection of the assistance accessory to the flange previously connected to the outer surface of said ventricular wall, the distal end of the assistance accessory then being inserted into the opening that is formed.

As is illustrated in FIG. 6, with this second flange 25 being pressed against the outer surface of the ventricular wall, it comprises at least one stub 35 positioned on its lateral wall, the connection head 26 of the assistance accessory 22 having, for each stub 35, a coupling groove 36 placed on its edge and configured to receive this corresponding stub. More precisely, each groove 36 opens out at the distal end of this connection head 26, in such a way that, with the latter partially covering the second flange 25 of the anchoring ring, each stub 35 is engaged in its corresponding groove.

Each groove 36 also has the same curved shape so that, by rotation of the assistance accessory 22 around the coring axis, this assistance accessory 22 is locked on the second flange 25.

This assistance accessory 22 also has a sealing element for sealing the assembly composed of connection head 26 and second flange 25, when the one or more stubs have been brought to the bottom of their corresponding groove on the connection head 26.

Figure 7:
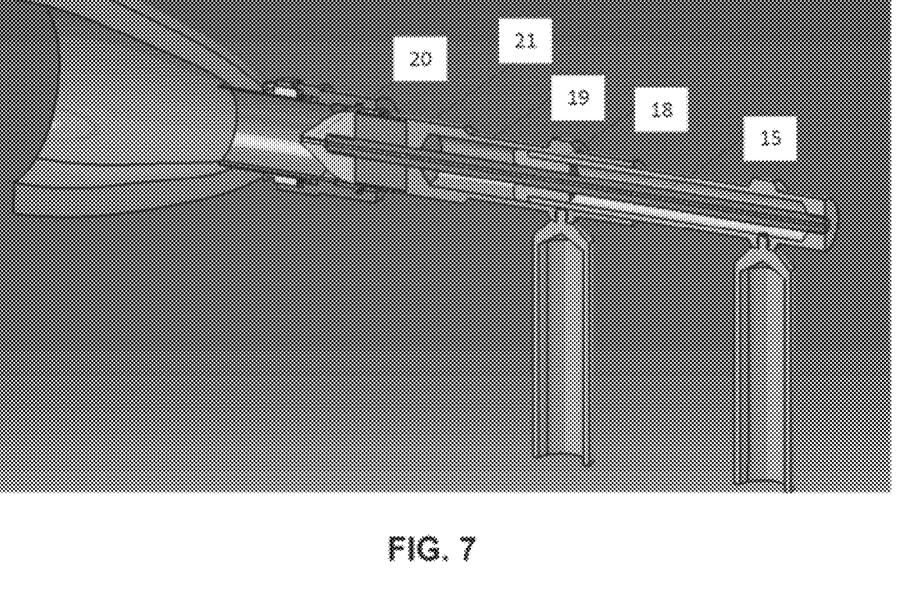
FIG. 7 is a longitudinal sectional view of the assembly from FIG. 2 and of the apex of the heart, the coring device being in the course of being withdrawn, the distal end of the assistance accessory, inserted in the formed opening, being exposed.

FIG. 7 is a sectional view of the coring device, the coring head being set back from the opening made in the ventricular wall, and, more precisely, being placed in the internal housing of the body of the coring device. The sheath 23 of the assistance accessory 22 has been inserted through this opening into the ventricular chamber, and the connection head 26 is connected to the second flange 25 of the anchoring ring outside the heart. The practitioner can then withdraw the coring device 10 without risking a displacement of the assistance accessory 22 from the opening made in the ventricular wall.

The sheath 23 of this assistance accessory 22 makes it possible to keep this opening fully accessible in order to ensure the free passage of the anchoring ring part comprising a tubular portion 27 and, at the distal end thereof, a self-expanding membrane 24 in its first configuration.

Figure 8:
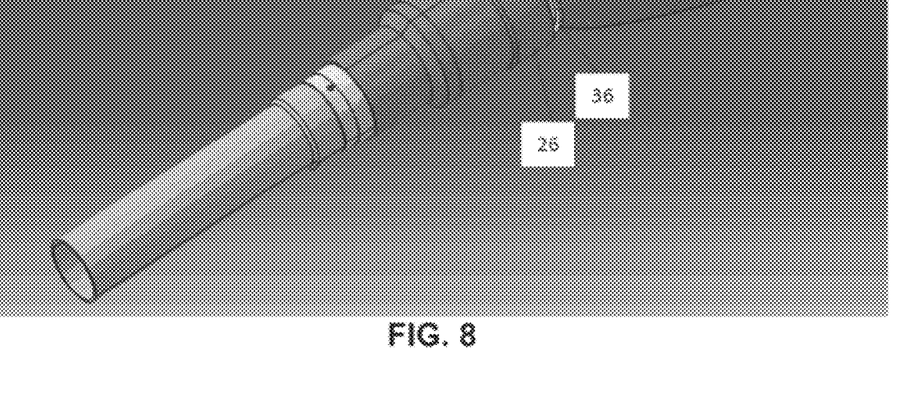
FIG. 8 is a perspective view of the assistance accessory from FIG. 2 connected to a flange rigidly connected to the apex of the heart, a part of an anchoring ring having a flange in its deformed configuration being inserted into this assistance accessory by means of a pusher device.
Figure 9:
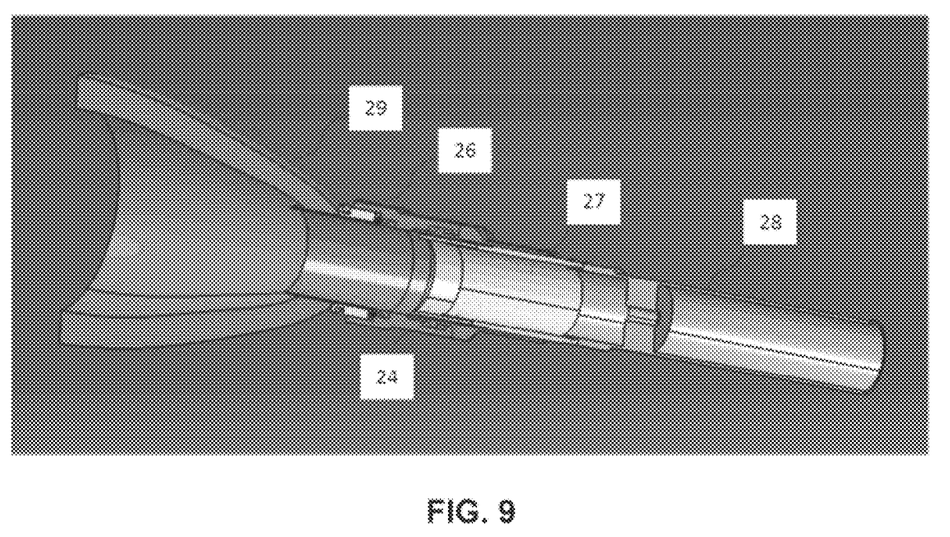
FIG. 9 is a longitudinal sectional view of the elements illustrated in FIG. 8.

This withdrawal of the coring device 10 causes the first loss of leaktightness at the ventricular wall, such that the practitioner must quickly connect to this hollow accessory a pusher device 28 carrying this anchoring ring part for the insertion of its end into the ventricular chamber 29.

Figure 10:
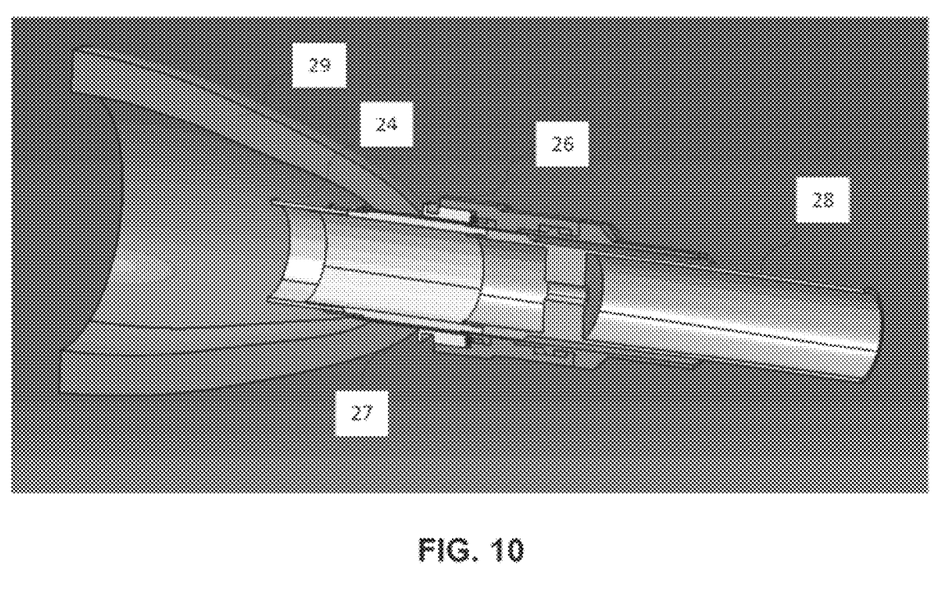
FIG. 10 is a longitudinal sectional view of the elements illustrated in FIG. 8, the flange in its deformed configuration being inserted into the ventricular chamber by means of the pusher device.
Figure 11:
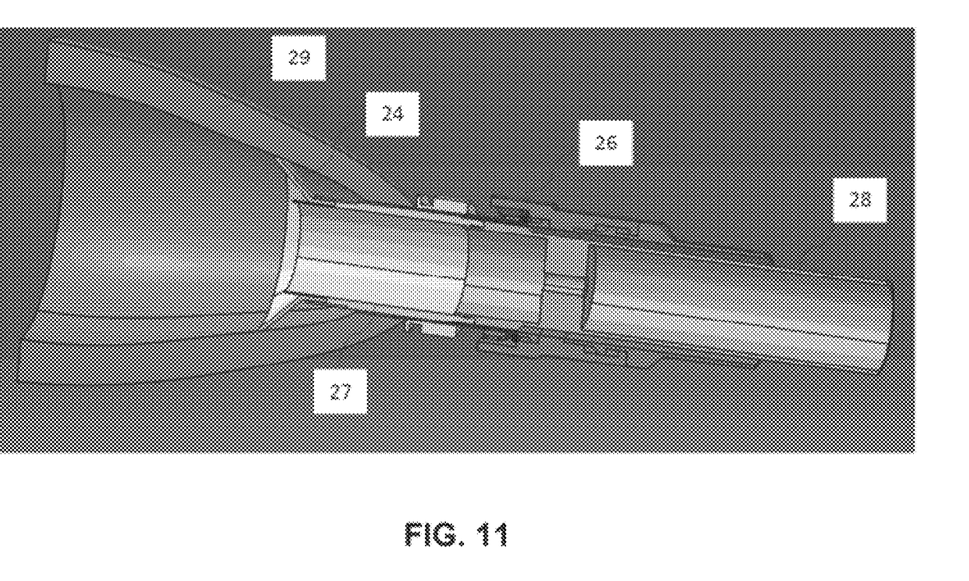
FIG. 11 is a longitudinal sectional view of the elements illustrated in FIG. 8, the flange being in its initial configuration in order to define a collar, the placement assistance accessory having been disconnected from the flange mounted on the outer surface of the ventricular wall and being in the course of being withdrawn.

Having inserted the self-expanding membrane 24 into this ventricular chamber, and said membrane having adopted its second configuration in which it defines a flange, or collar, extending radially from the tubular portion 27, the practitioner draws back the pusher device 28 in order to press this flange against the inner face of the ventricular wall 29 of the beating heart.

Figure 12:
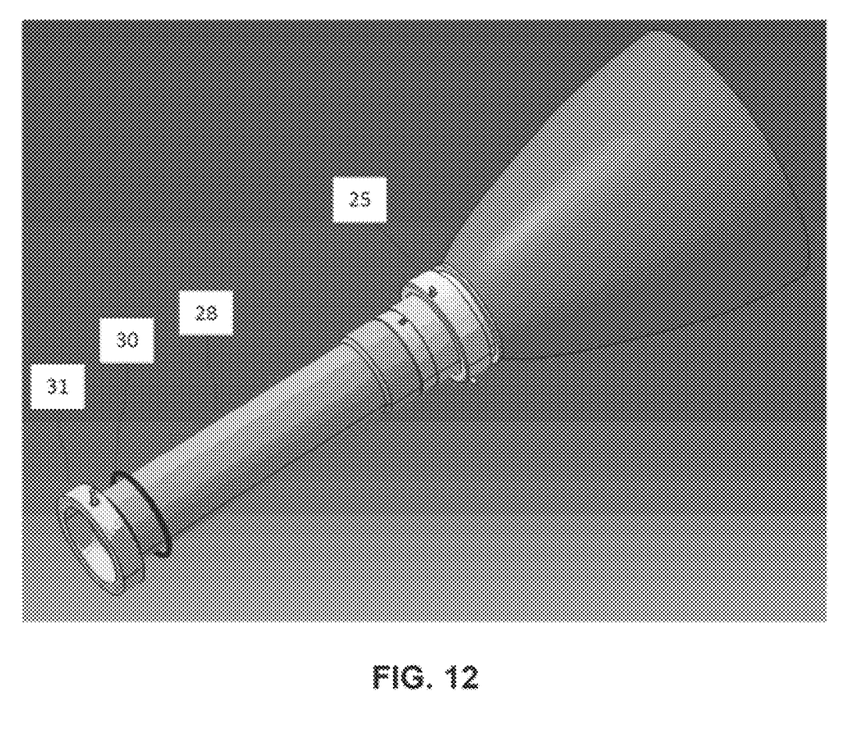
FIG. 12 is a perspective view of the elements illustrated in FIG. 8, the assistance accessory having been withdrawn, a seal and a nut being engaged on the pusher device in order to lock the anchoring ring in position.

Thus, with the two flanges 24, 25 being pressed on either side against this ventricular wall 29, the practitioner simply has to engage a sealing element 30 such as an O-ring seal and a clamping means 31 on the pusher device 28 and slide them along the outer surface of this pusher device 28 in order to lock the anchoring ring in position. This clamping means 31 finalizes the assembly of the anchoring ring by blocking any movement of the flanges 24, 25 relative to each other. This results in a strong mechanical connection of the anchoring ring and the apex of the heart and also its sealing.

Figure 13:
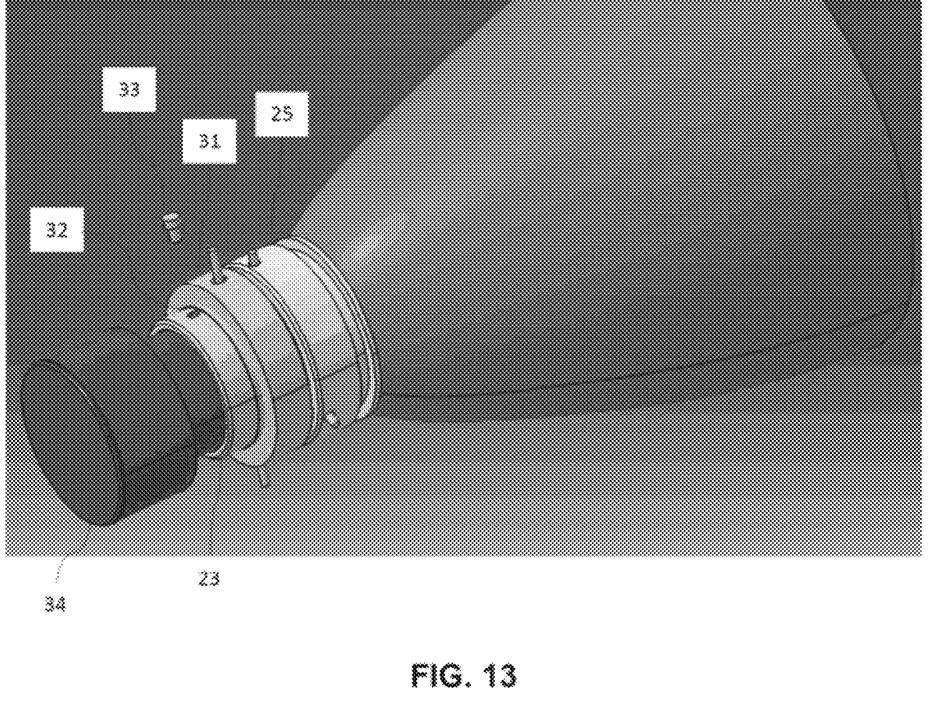
FIG. 13 is a perspective view of the anchoring ring from FIG. 12 mounted in its opening and supporting a cardiac pump.

This clamping means 31 can be a nut if the outer surface of the tubular portion 27, or hollow body, has a thread or, as is illustrated in FIG. 13, a clamping ring. The latter presses the sealing element 30 against the second flange 25 connected to the outer surface of the ventricular wall 29.

Advantageously, the assembly composed of tubular portion 27 and self-expanding membrane 24 comprises a second sealing element comprising an anti-reflux valve (not shown) placed in the internal channel delimited by this tubular portion 27. By way of example, it is a self-repairing membrane, also called a self-sealing membrane, integrated in the internal channel delimited by the tubular portion 27, or hollow body, of the anchoring ring. This anti-reflux valve prevents any leakage of blood through this internal channel. After removal of the coring device, it thus makes it possible to restore the leaktightness by placing the anchoring device on the heart.

Purely by way of illustration, this anti-reflux valve is made of silicone.

This clamping ring 31 has, on its lateral wall, an orifice 32 receiving a fastener 33 for locking in position a cardiac pump 34 inserted into the internal channel delimited by the hollow body of the anchoring ring, the distal end of this cardiac pump 34 being engaged in the ventricular chamber of the beating heart. Upon removal of the cardiac pump 34 from the heart, for example for handling, received in the tubular portion 27, this second sealing element closes and becomes leaktight again.

What is claimed is:

1. A coring device for forming an opening in a tissue wall, this device comprising:
    a body having a longitudinal axis, said body having a proximal end and a distal end, said body having an internal housing,
    a coring head having a transection blade, this head being movable between a rest position and an actuated position, said transection blade being an annular cutting member mounted on the proximal end of said coring head and being configured to cut a cylindrical mass of tissue when displaced from the actuated position back to the rest position,
    an actuation mechanism for moving said head between said positions, said mechanism having an actuation rod, at one end of which said movable head is placed, and the distal end of said body forms a support for a surgical tool, this tool support being configured
        to receive a hollow surgical tool by positive engagement and to support this tool, this tool surrounding the distal end of said body when it is placed A on said tool support, by being coaxial with said coring axis, and
        to permit linear guiding of said surgical tool during movement of the coring device, along the longitudinal axis and in that,
    said tool support has an outer peripheral wall which is tubular and of a diameter equal to or substantially equal to the diameter of said transection blade so the outer surface of the transection blade is flush, or substantially flush, with the outer peripheral wall of the tool support, and in that,
    said device comprises a lumen extending through at least the proximal end of said body, said actuation rod and said coring head in order to allow the passage of a flexible guide element, said coring device comprising such a flexible guide element.

2. The device as claimed in claim 1, wherein with said tissue wall being a wall of a beating heart intended to receive an anchoring device of a cardiac pump comprising a flange, or collar, intended to be pressed against the outer surface of said wall of the beating heart, the length of said tool support is configured to be at least equal to the sum of the thickness of said tissue wall and the thickness, or longitudinal dimension, of said flange, or collar, intended to be placed against the outer surface of the wall of said heart.

3. The device as claimed in claim 1, wherein said device has one part of an indexing means configured to align said surgical tool on said support.

4. The device as claimed in claim 1, wherein said device has a stop configured for stopping the movement of said surgical tool along said longitudinal axis and in the direction of said proximal end, such that the surgical tool remains positioned on said tool support.

5. The device as claimed in claim 1, wherein said body has two body parts engaged one inside the other, a first body part being movable in translation relative to the other body part, such that its movement in and out of the other body part causes the translation movement of said coring head.

6. The device as claimed in claim 5, wherein each body part has a gripping handle.

7. The device as claimed in claim 5, wherein said actuation mechanism comprises a guide carriage supporting said actuation rod and received in said inner housing, this housing being configured to form a guide rail for translation of said guide A carriage, said guide carriage being rigidly connected to said first body part.

8. An assembly for placing a tool or a surgical accessory in a tissue wall, wherein the assembly comprises:
    a coring device as claimed in claim 1, and
    a hollow surgical tool or accessory configured to be engaged on the distal end of said coring device.

9. The assembly as claimed in claim 8, wherein said surgical tool or accessory has, at its distal end, a tubular or substantially tubular portion configured to maintain the shape and diameter of an opening formed by coring in the tissue wall.

10. The assembly as claimed in claim 9, wherein said tubular or substantially tubular portion is configured to have a length at least equal to the thickness of the tissue wall.

11. The assembly as claimed in claim 8, wherein with the body of the coring device having one part of an indexing means, said hollow surgical tool or accessory has a complementary part of this indexing means, in order to align said surgical tool or accessory on said tool support.

12. The assembly as claimed in claim 8, wherein said hollow surgical tool or accessory is a tool for assisting the placement of a device for anchoring a cardiac pump through an opening made by coring in a wall of a heart, wherein said hollow surgical tool or accessory delimits an internal channel configured for the passage of an anchoring device having a diameter substantially equal to the diameter of this opening.

13. The assembly as claimed in claim 12, wherein for flange, or collar, being intended to be placed against the outer surface of the wall of said heart, and with this flange comprising at least one protrusion, or stub, placed on its lateral face, said hollow surgical tool or accessory comprises an open groove configured to receive a protrusion, or stub, said groove being configured to ensure, by rotation of said surgical tool about the longitudinal axis, a locking of said surgical tool on said flange or collar.

* * * * *

UNITED STATES PATENT AND TRADEMARK OFFICE
CERTIFICATE OF CORRECTION

| | |
|---|---|
| PATENT NO. | : 11,925,382 B2 |
| APPLICATION NO. | : 17/057211 |
| DATED | : March 12, 2024 |
| INVENTOR(S) | : Mascarell et al. |

It is certified that error appears in the above-identified patent and that said Letters Patent is hereby corrected as shown below:

On the Title Page

Item (73) Assignee should be "FINEHEART"

In the Claims

Column 11, Claim 13, Line 7, after "for" insert --a--

Signed and Sealed this
Nineteenth Day of November, 2024

Katherine Kelly Vidal
*Director of the United States Patent and Trademark Office*